United States Patent [19]

Macchio et al.

[11] Patent Number: 4,837,011

[45] Date of Patent: Jun. 6, 1989

[54] COSMETIC POWDER EMPLOYING SPHERICAL SILICA PARTICLES

[75] Inventors: Ralph A. Macchio, Monsey; Ivonne Brown, Roosevelt; Marlene Tietjen, New York, all of N.Y.

[73] Assignee: Revlon, Inc., New York, N.Y.

[21] Appl. No.: 256,210

[22] Filed: Oct. 11, 1988

Related U.S. Application Data

[63] Continuation of Ser. No. 93,925, Sep. 8, 1987, abandoned.

[51] Int. Cl.$^4$ ............................................. A61K 7/035
[52] U.S. Cl. ........................................ 424/69; 424/63; 424/64; 514/789; 514/943
[58] Field of Search ............................ 424/63, 64, 69; 514/789, 943

[56] References Cited

U.S. PATENT DOCUMENTS 4,606,914  8/1986  Miyoshi ............................... 424/64

FOREIGN PATENT DOCUMENTS 61-174103  8/1986  Japan .

Primary Examiner—Thurman K. Page
Assistant Examiner—P. Prater

[57] ABSTRACT

Disclosed is a novel cosmetic powder composition exhibiting superior smoothness and adhesion to the skin, comprising in its preferred version a combination of ultrafine silica, talc coated with acylamino acid, sericite, polyethylene, and a novel binder comprising a combination of polydimethylsiloxane, distearyl malate and pentahydrosqualene.

9 Claims, No Drawings

COSMETIC POWDER EMPLOYING SPHERICAL SILICA PARTICLES

This application is a continuation of application Ser. No. 093,925, filed Sept. 8, 1987, now abandoned.

BACKGROUND OF THE INVENTION

The present invention relates to cosmetic powders, that is, compositions having an ultrafine particle size adapted for application to the skin of a wearer. The invention overcomes the tendency of many previously known cosmetic powders to appear excessively dry following application to the skin. Other advantages will be apparent in the following description.

BRIEF SUMMARY OF THE INVENTION

The present invention comprises a cosmetic powder composition comprising:
 (a) essentially spherical silica having an average particle size of 6 to 20 microns, in an amount up to 15 parts by weight;
 (b) 25 to 80 parts by weight of sericite or sericite the surfaces of which are coated with up to 5 percent by weight of the sericite of mineral oil or polydimethylsiloxane having a viscosity of 5 to 100 centistokes;
 (c) 1 to 5 parts by weight of polydimethylsiloxane having a viscosity of 5 to 100 centistokes; and
 (d) 1 to 5 parts by weight of isostearyl malate, diisostearyl malate, or a mixture thereof.

The composition can further comprise one or more of the following: up to 5 wt.% of one or more waxes selected from the group consisting of candelilla, microcrystalline wax, and carnauba;

20 to 70 parts by weight of talc the surfaces of which are coated with 0.5 to 10 percent, by weight of the talc, of one or more metal salts of an N-acylamino acid having formula (I), (II), or (III):

$$(RCO-NHCH(COO)CH_2CH_2COO)_{1-3}M_{1-2} \quad (I)$$

$$(RCO-N(CH_3)CH_2CH_2COO)_{1-4}M \quad (II)$$

$$(RCO-N(CH_3)CH_2COO)_{1-4}M \quad (III)$$

wherein RCO- denotes a residue of capric, lauric, myristic, palmitic, stearic, or oleic acid; and M is an atom of aluminum, magnesium, calcium, zinc, zirconium, or titanium;

1 to 5 parts by weight of squalene, of pentahydrosqualene, or a mixture thereof; and/or 5 to 15 parts by weight of polyethylene.

DETAILED DESCRIPTION OF THE INVENTION

The present invention is useful as an ultrasmooth face powder which possess excellent adherence to the skin, and extremely smooth and velvety application which enhances the attraction of the product to the user. The powder can be sold loose or pressed into pans through conventional pressing techniques. It can be applied from a compact or equivalent dispenser, with an applicator of conventional design, or simply with the user's finger.

In the following description, each of the desired components of the powder composition of the present invention is described separately. However, it should be clearly understood that the present invention resides not only in the selection and amount of the particular components described, but also in the highly advantageous and unprecedented combination of such ingredients in the composition of the present invention.

The powder composition of the present invention comprises silica, having an average particle size of 6 to 20 microns. The particles of silica are preferably spherical or nearly spherical in shape. Silica of this type, and its preparation, are described in Japanese Laid-open Patent Application No. 61-174103, the disclosure of which is hereby incorporated herein. This component, in combination with the other ingredients of the claimed product, contributes a high degree of slip to the final product, thereby providing ease and smoothness of application to the skin. At the same time, the product provides excellent adhesion to the skin, without becoming dry or caked-looking following application. These properties are believed to be due to the unusually low absorbency of the silica, even at silica contents as high as 15 wt.% of the powder composition. This component can be present in amounts up to about 15 parts by weight of the composition, and preferably from about 6 to about 15 parts by weight.

The composition of the present invention also contains sericite or, preferably, surface-modified sericite. Sericite is a naturally occurring mica-like substance. Preferably, the sericite surface is modified by coating it with up to 5% by weight of the sericite with mineral oil, with polydimethylsiloxane of the type having a viscosity of 5 to 100 centistokes, or with a mixture of mineral oil and such a polydimethylsiloxane. The sericite (or surface-modified sericite), in combination with the other ingredients of the present invention, provides the cosmetic powder with superior softness and smoothness. In particular, the high smoothness of the powder in the presence of both sericite and the silica is particularly unexpected and advantageous. This component also provides superior skin adhesion and a feeling of water repellence in addition to smooth slip and feel which enhance the aesthetic attractiveness of this product to the user. This component is present in an amount comprising 25 to 80 parts by weight of the composition.

The aforementioned ingredients are preferably contained in a multi-component binder which contributes to the smooth, creamy feel of the product as well as to the excellent appearance of the product on the skin. The binder comprises several ingredients as follows:

One such ingredient is 1 to 5 parts by weight of mono-isostearyl malate or diisostearyl malate. This component contributes emolliency and high slip to the composition, without causing excessive compacting of the other ingredients.

Another component is 1 to 5 parts by weight polydimethylsiloxane fluid, by which is meant a silicone fluid of the formula $(CH_3)_3Si-(O-Si(CH_3)_2)_n-Si(CH_3)_3$ wherein n has a value such that the viscosity of the polydimethylsiloxane is in the range of 5 to 300 centistokes. Preferably, the viscosity is not above 100 centistokes. This ingredient also gives the product highly attractive slip as well as providing water repellence and coating of the other ingredients of the composition.

The composition of the present invention can also comprise any of a number of conventional cosmetically acceptable ingredients. Among these are ultraviolet absorbers (sunscreens), which protect the skin from exposure to ultraviolet radiation. Examples of such ultraviolet absorbers include alkyl salts of PABA (para-amino benzoic acid) such as octyldimethyl PABA.

Equivalent ultraviolet absorbers can readily be determined by those of ordinary skill in this art by consultation with appropriate cosmetic dictionaries. Other optional ingredients which may be desired include inorganic, organic, or surface-treated inorganic pigments, in an amount up to 80 wt.% of the cosmetic powder. Examples of acceptable pigments include titanium oxide, zinc oxide, polyethylene, talc, zirconium oxide, iron oxide (red, yellow, or black), mica, ultramarine blue, chromium oxide, and bismuth oxychloride. Examples of acceptable organic pigments are all FDA-approved dyes and lakes. The composition can also contain a small but effective amount, generally up to 0.5 wt.%, of one or more preservatives such as methyl or propylparaben.

The composition of the present invention can also contain 20 to 70 parts by weight, and more preferably 20 to 40 parts by weight, of an inorganic platelet-type material which is coated with acylamino acid salt. Preferably, the inorganic material is talc, although other materials can also be added such as kaolin, sericite, mica, and the like. The surface coating, which is preferably present in an amount of 0.5 to 10% by weight of the talc or other coated inorganic material, comprises one or more metal salts preferably of an N-acylamino acid having any of the following formulas (I), (II), or (III):

$$(RCO-NHCH(COO)CH_2CH_2COO)_{1-3}M_{1-2} \quad (I)$$

$$(RCO-N(CH_3)CH_2CH_2COO)_{1-4}M \quad (II)$$

$$(RCO-N(CH_3)CH_2COO)_{1-4}M \quad (III)$$

In the above formulas, RCO- denotes a residue of capric, lauric, myristic, palmitic, stearic, or oleic acid and M is an atom of aluminum, magnesium, calcium, zinc, zirconium, or titanium. This component, and methods for its preparation, are disclosed in U.S. Pat. No. 4,606,914 the disclosure of which is hereby incorporated herein. This component of the present composition, in combination with the other ingredients, provides smooth applicability, and freedom from drying or glazing after application to the skin. This component in the present invention also appears to enhance moisture retention of the skin. The average particle size of this component is preferably 1 to 20 microns.

The present composition can also comprise 5 to 15 parts by weight of polyethylene, when the powder is to be pressed into a pressed powder. This ingredient, in combination with the other ingredients of the present composition, provides highly advantageous binding of the several ingredients of the composition, and also provides a smooth, creamy feel to the product upon application to the skin. Preferably, the polyethylene particle size is in the range of 5 to 20 microns.

The composition can also contain 1 to 5, preferably 3 to 5, parts by weight of pentahydrosqualene and/or squalene. This ingredient provides excellent wetting properties, as well as emolliency. This ingredient also provides a high degree of solvency for the other ingredients of the composition, thereby contributing to the product's high degree of homogeneity. It has also been found that this ingredient permits the formulator to incorporate any of several optional waxes, which further contribute to the smooth feel and attractive appearance of the cosmetic powder. Among such waxes are candelilla, microcrystalline wax, or carnauba wax. The amount of such wax should not exceed about 5 wt.%, and preferably not exceed about 3 wt.%, of the composition.

The compositions of the present invention can be prepared simply by mixing together and pulverizing all the dry ingredients, separately heating (e.g. up to 20°–75° C.) and blending the components of the binder (isostearyl malate and/or diisostearyl malate; polydimethylsiloxane; and optional pentahydrosqualene and/or wax or waxes, and/or ultraviolet absorbers), then spraying the latter mixture into the former mixture while stirring, and then continuing to stir to achieve a completely uniform mixture of all ingredients. The resulting mixture is then pulverized.

Examples of formulations conforming to the above description are as follows (all amount in weight percent):

| Component | Example 1 | Example 2 |
| --- | --- | --- |
| Zinc Stearate | 4.0 | 4.0 |
| Spherical Silica (6–20 microns) | 6.0 | 5.0 |
| Sericite | 34.0 | 34.0 |
| Talc | 28.3 | 28.6 |
| Polyethylene | 10.0 | 10.0 |
| Calcium silicate | — | 1.0 |
| Pigments (bismuth oxychloride, iron oxides, ultramarine blue) | 5.55 | 5.25 |
| Methyl paraben | 0.3 | 0.3 |
| Propyl paraben | 0.1 | 0.1 |
| Pentahydrosqualene | 4.0 | 4.0 |
| Diisostearyl malate | 2.4 | 2.4 |
| Polydimethylsiloxane | 4.35 | 4.35 |
| Octyldimethyl PABA | 1.0 | 1.0 |

What is claimed is:

1. A cosmetic powder composition comprising:
   (a) essentially spherical silica having an average particle size of 6 to 20 microns, in an amount up to 15 wt.% of the composition;
   (b) 25 to 80 parts by weight of material selected from the group consisting of sericite, sericite coated with mineral oil or polydimethylsiloxane having a viscosity of 5 to 100 centistokes wherein the coating comprises up to 5% by weight of the sericite and mixtures thereof;
   (c) 1 to 5 parts by weight of polydimethylsiloxane having a viscosity of 5 to 100 centistokes; and
   (d) 1 to 5 parts by weight of material selected from the group consisting of isostearyl malate, diisostearyl malate, and mixtures thereof.

2. The composition of claim 1 and further comprising up to 5 wt.% of one or more waxes selected from the group consisting of candelilla, microcrystalline wax, and carnauba.

3. The composition of claim 1 and further comprising 20 to 70 parts by weight of talc coated with 0.5 to 10 percent, by weight of the talc, of one or more metal salts of an N-acylamino acid having formula (I), (II), or (III):

$$(RCO-NHCH(COO)CH_2CH_2COO)_{1-3}M_{1-2} \quad (I)$$

$$(RCO-N(CH_3)CH_2CH_2COO)_{1-4}M \quad (II)$$

$$(RCO-N(CH_3)CH_2COO)_{1-4}M \quad (III)$$

wherein RCO- denotes a residue of capric, lauric, myristic, palmitic, stearic, or oleic acid; and M is an atom of aluminum, magnesium, calcium, zinc, zirconium, or titanium.

4. The composition of claim 1 and further comprising 1 to 5 parts by weight of material selected from the group consisting of squalene, pentahydrosqualene, and mixtures thereof.

5. The composition of claim 1 and further comprising 5 to 15 parts by weight of polyethylene.

6. The composition of claim 1 and further comprising 20 to 70 parts by weight of talc coated with 0.5 to 10 percent, by weight of the talc, of one or more metal salts of an N-acylamino acid having formula (I), (II), or (III):

$$(RCO-NHCH(COO)CH_2CH_2COO)_{1-3}M_{1-2} \qquad (I)$$

$$(RCO-N(CH_3)CH_2CH_2COO)_{1-4}M \qquad (II)$$

$$(RCO-N(CH_3)CH_2COO)_{1-4}M \qquad (III)$$

wherein RCO- denotes a residue of capric, lauric, myristic, palmitic, stearic, or oleic acid; and M is an atom of aluminum, magnesium, calcium, zinc, zirconium, or titanium; and 1 to 5 parts by weight of material selected from the group consisting of squalene, pentahydrosqualene, and mixtures thereof.

7. The composition of claim 1 and further comprising 20 to 70 parts by weight of talc coated with 0.5 to 10 percent, by weight of the talc, of one or more metal salts of an N-acylamino acid having formula (I), (II), or (III):

$$(RCO-NHCH(COO)CH_2CH_2COO)_{1-3}M_{1-2} \qquad (I)$$

$$(RCO-N(CH_3)CH_2CH_2COO)_{1-4}M \qquad (II)$$

$$(RCO-N(CH_3)CH_2COO)_{1-4}M \qquad (III)$$

wherein RCO- denotes a residue of capric, lauric, myristic, palmitic, stearic, or oleic acid; and M is an atom of aluminum, magnesium, calcium, zinc, zirconium, or titanium; and 5 to 15 parts by weight of polyethylene.

8. The composition of claim 1 and further comprising 1 to 5 parts by weight of material selected from the group consisting of squalene, pentahydrosqualene, and mixtures thereof; and 5 to 15 parts by weight of polyethylene.

9. The composition of claim 1 and further comprising 20 to 70 parts by weight of talc coated with 0.5 to 10 percent, by weight of the talc, of one or more metal salts of an N-acylamino acid having formula (I), (II), or (III):

$$(RCO-NHCH(COO)CH_2CH_2COO)_{1-3}M_{1-2} \qquad (I)$$

$$(RCO-N(CH_3)CH_2CH_2COO)_{1-4}M \qquad (II)$$

$$(RCO-N(CH_3)CH_2COO)_{1-4}M \qquad (III)$$

wherein RCO- denotes a residue of capric, lauric, myristic, palmitic, stearic, or oleic acid; and M is an atom of aluminum, magnesium, calcium, zinc, zirconium, or titanium;

1 to 5 parts by weight of material selected from the group consisting of squalene, pentahydrosqualene, and mixtures thereof; and 5 to 15 parts by weight of polyethylene.

* * * * *